United States Patent
Matsumoto et al.

(10) Patent No.: US 8,590,464 B2
(45) Date of Patent: Nov. 26, 2013

(54) PULVERIZED COAL CONCENTRATION ADJUSTMENT APPARATUS AND PULVERIZED COAL COMBUSTION BOILER

(75) Inventors: Shinji Matsumoto, Nagasaki (JP); Tsugio Yamamoto, Nagasaki (JP); Masahiko Taniguchi, Nagasaki (JP); Kazuhiro Takeuchi, Nagasaki (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 1166 days.

(21) Appl. No.: 12/443,526

(22) PCT Filed: Mar. 19, 2008

(86) PCT No.: PCT/JP2008/055122
§ 371 (c)(1),
(2), (4) Date: Mar. 30, 2009

(87) PCT Pub. No.: WO2008/123109
PCT Pub. Date: Oct. 16, 2008

(65) Prior Publication Data
US 2010/0006012 A1    Jan. 14, 2010

(30) Foreign Application Priority Data
Mar. 26, 2007    (JP) .................................. 2007-079778

(51) Int. Cl.
*F23K 3/02*    (2006.01)
(52) U.S. Cl.
USPC .......................................... 110/263; 110/310
(58) Field of Classification Search
USPC ............. 110/104 R, 106, 260, 261, 263, 264, 110/265, 347
See application file for complete search history.

(56) References Cited

U.S. PATENT DOCUMENTS

| | | | |
|---|---|---|---|
| 6,976,440 B2 * | 12/2005 | Ohtani et al. ................ | 110/310 |
| 7,013,815 B2 * | 3/2006 | Levy et al. .................. | 110/309 |

(Continued)

FOREIGN PATENT DOCUMENTS

| | | |
|---|---|---|
| JP | 59-32933 A | 2/1984 |
| JP | 61-141535 U | 9/1986 |

(Continued)

OTHER PUBLICATIONS

International Search Report of PCT/JP2008/055122, Mailing Date of Jun. 17, 2008.

(Continued)

*Primary Examiner* — Kenneth Rinehart
*Assistant Examiner* — David J Laux
(74) *Attorney, Agent, or Firm* — Westerman, Hattori, Daniels & Adrian, LLP (57) ABSTRACT

To achieve an improvement in concentration distribution in a vertical direction at an inlet of a pulverized coal distributor and uniformly distribute pulverized coal to respective pulverized coal burners. A pulverized coal distributor and a gas-particle flow adjustment device provided on an upstream side of the pulverized coal distributor and at a bottom in a pulverized coal pipe to adjust pulverized coal to branch pipes in concentration are provided, the gas-particle flow adjustment device comprises a plate-shaped member provided along a substantially overall width of the pulverized coal pipe to have a substantially rectangular shape as viewed in plan view, a front edge of the gas-particle flow adjustment device is mounted pivotally to a bottom surface of the pulverized coal pipe, and an angle formed between an upper surface of the gas-particle flow adjustment device and a bottom surface of the pulverized coal pipe can be automatically adjusted on the basis of signals from flow sensors mounted to the respective branch pipes.

2 Claims, 6 Drawing Sheets

(56) References Cited

U.S. PATENT DOCUMENTS

| | | | |
|---|---|---|---|
| 7,341,007 B2 * | 3/2008 | Vatsky | 110/104 B |
| 2004/0231572 A1 | 11/2004 | Ohtani et al. | |
| 2007/0000416 A1 * | 1/2007 | Widmer et al. | 110/342 |
| 2007/0095260 A1 * | 5/2007 | John | 110/342 |

FOREIGN PATENT DOCUMENTS

| | | | |
|---|---|---|---|
| JP | 63-271019 A | | 11/1988 |
| JP | 7-103452 A | | 4/1995 |
| JP | 9-112876 A | | 5/1997 |
| JP | 9-196314 A | | 7/1997 |
| JP | 11-287433 A | | 10/1999 |
| JP | 11287433 A | * | 10/1999 |
| JP | 2004-301415 A | | 10/2004 |
| JP | 2005-241107 A | | 9/2005 |
| JP | 2006-102666 A | | 4/2006 |
| WO | 03/048643 A1 | | 6/2003 |

OTHER PUBLICATIONS

Mexican Office Action dated Apr. 11, 2013, issued in corresponding Mexican Patent Application No. MX/a/2009/002940.

Vietnamese Decision to Grant dated Jan. 25, 2013, issued in corresponding Vietnamese Patent Application No. 1-2009-00592, with explanation of relevance.

* cited by examiner

PULVERIZED COAL CONCENTRATION ADJUSTMENT APPARATUS AND PULVERIZED COAL COMBUSTION BOILER

TECHNICAL FIELD

The present invention relates to a pulverized coal concentration adjustment apparatus for adjustment of pulverized coal supplied to a plurality of pulverized coal burners mounted to a kiln wall of a pulverized coal combustion boiler, and a pulverized coal combustion boiler using the same.

BACKGROUND ART

As a pulverized coal combustion boiler, in which pulverized coal pulverized in a coal mill (mill apparatus) is supplied to a plurality of pulverized coal burners mounted to a kiln wall and burnt by the pulverized coal burners, one disclosed in, for example, Patent Citation 1 is known.
Patent Citation 1: Japanese Unexamined Patent Application, Publication No. 2006-102666

DISCLOSURE OF INVENTION

By the way, in such pulverized coal combustion boiler, pulverized coal pulverized in a coal mill is pneumatically conveyed in a pulverized coal pipe. Since pulverized coal is large in mass as compared with an air and has a tendency of gravitational sedimentation, pulverized coal flowing in a lower portion of a pulverized coal pipe in the pulverized coal pipe is heightened in concentration. Therefore, the concentration distribution of pulverized coal in a vertical direction becomes non-uniform at an inlet of a pulverized coal distributor provided downstream of the pulverized coal pipe, so that pulverized coal fed to respective pulverized coal burners through left and right branch pipes from respective flow passages of the pulverized coal distributor is distributed differently. In this manner, pulverized coal fed to the respective pulverized coal burners is distributed differently whereby there is a fear that a pulverized coal combustion boiler is made worse (an increase in NOx or unburned coal) and boiler water tubes become non-uniform in temperature.

The invention has been thought of in view of the situation described above and has its object to provide a pulverized coal concentration adjustment apparatus, which can achieve an improvement in concentration distribution in a vertical direction at an inlet of a pulverized coal distributor and uniformly distribute pulverized coal to respective pulverized coal burners, and a pulverized coal combustion boiler.

The invention adopts the following means in order to solve the problem described above.

A pulverized coal concentration adjustment apparatus according to the invention comprises a pulverized coal distributor, of which an upstream end is connected to a pulverized coal pipe, through which pulverized coal is pneumatically conveyed to flow, and a downstream end is connected to a plurality of branch pipes, and which distributes and pneumatically conveys the pulverized coal to the respective branch pipes through flow passages in plural stages, and a gas-particle flow adjustment device provided on an upstream side of the pulverized coal distributor and at a bottom in the pulverized coal pipe to adjust pulverized coal to the branch pipes in concentration, and the gas-particle flow adjustment device comprises a plate-shaped member provided along a substantially overall width of the pulverized coal pipe to have a substantially rectangular shape as viewed in plan view, a front edge of the gas-particle flow adjustment device is mounted pivotally to a bottom surface of the pulverized coal pipe, and an angle formed between an upper surface of the gas-particle flow adjustment device and a bottom surface of the pulverized coal pipe can be automatically adjusted on the basis of signals from flow sensors mounted to the respective branch pipes.

With the pulverized coal concentration adjustment apparatus according to the invention, an angle of an upper surface of the plate-shaped member is automatically adjusted on the basis of signals from the flow sensors mounted to the respective branch pipes. Therefore, with the pulverized coal concentration adjustment apparatus, pulverized coal passing in, for example, the respective branch pipes can be made substantially equal (substantially uniform) in concentration to each other, and pulverized coal fed to the respective branch pipes positioned downstream of the pulverized coal distributor and the respective pulverized coal burners can be uniformly distributed, so that it is possible to improve the combustion quality (reduction in NOx and unburned coal), thus enabling making boiler water tube temperatures uniform.

A pulverized coal concentration adjustment apparatus according to the invention comprises a pulverized coal pipe, through which pulverized coal is pneumatically conveyed to flow, and a pulverized coal distributor, of which an upstream end is connected to the pulverized coal pipe and a downstream end is connected to a plurality of branch pipes, and which distributes and pneumatically conveys the pulverized coal to the respective branch pipes through flow passages in plural stages, and a downstream end of the pulverized coal pipe is formed to arrange the pulverized coal distributor in a location, in which a distance from an elbow portion of the pulverized coal pipe is equal to or less than 10 times an inside diameter of the pulverized coal pipe, more preferably, in that range, in which a distance from the elbow portion of the pulverized coal pipe is three times to five times the inside diameter of the pulverized coal pipe.

With the pulverized coal concentration adjustment apparatus according to the invention, pulverized coal flowing in a lower portion of the pulverized coal pipe on the upstream side of the elbow flows along an inner wall surface of the elbow positioned radially outward to be directed upward from the lower portion of the pulverized coal pipe while being acted by a centrifugal force at the elbow. Consequently, the pulverized coal is rolled upward in the vicinity of an outlet (that is, in the vicinity of an inlet of the pulverized coal distributor) of the elbow to flow into the inlet of the pulverized coal distributor while being scattered upward.

Thereby, pulverized coal fed to the respective branch pipes positioned downstream of the pulverized coal distributor and the respective pulverized coal burners can be uniformly distributed, so that it is possible to improve the combustion quality (reduction in Nox and unburned coal), thus enabling making boiler water tube temperatures uniform.

A pulverized coal concentration adjustment apparatus according to the invention comprises a pulverized coal distributor, of which an upstream end is connected to a pulverized coal pipe, through which pulverized coal is pneumatically conveyed to flow, and a downstream end is connected to a plurality of branch pipes, and which distributes and pneumatically conveys the pulverized coal to the respective branch pipes through flow passages in plural stages, and a ribbon screw arranged in the pulverized coal pipe and downstream of an elbow portion of the pulverized coal pipe to impart a whirling flow to the pulverized coal.

With the pulverized coal concentration adjustment apparatus according to the invention, pulverized coal flowing in a lower portion of the pulverized coal pipe on the upstream side of the elbow flows along an inner wall surface of the elbow positioned radially outward while being acted by a centrifugal force at the elbow. Thereafter, the pulverized coal is given a whirling force (rotating force) when passing between a surface of the ribbon screw and an inner wall surface of a pulverized coal pipe positioned downstream of the elbow, and flows into an inlet of a pulverized coal distributor while being scattered radially outward.

Thereby, pulverized coal fed to respective branch pipes positioned downstream of the pulverized coal distributor and respective pulverized coal burners can be uniformly distributed, so that it is possible to improve the combustion quality (reduction in NOx and unburned coal), thus enabling making boiler water tube temperatures uniform.

A pulverized coal combustion boiler according to the invention comprises a pulverized coal concentration adjustment apparatus, which can uniformly distribute pulverized coal, which is fed to respective branch pipes positioned downstream of a pulverized coal distributor and respective pulverized coal burners, so that it is possible to improve the combustion quality (reduction in NOx and unburned coal), thus enabling making boiler water tube temperatures uniform.

The invention produces an effect that it is possible to achieve an improvement in concentration distribution in a vertical direction at an inlet of a pulverized coal distributor and to uniformly distribute pulverized coal to respective pulverized coal burners.

EXPLANATION OF REFERENCE

1: pulverized coal combustion boiler
13: pulverized coal pipe
13a: pulverized coal pipe
13b: pulverized coal pipe
13c: pulverized coal pipe
13d: pulverized coal pipe
17a: pulverized coal distributor
17b: pulverized coal distributor
17c: pulverized coal distributor
17d: pulverized coal distributor
18a: branch pipe
18b: branch pipe
19: pulverized coal concentration adjustment apparatus
20: kicker block (gas-particle flow adjustment device)
22: flow passage
31: pulverized coal concentration adjustment apparatus
32: elbow
33a: pulverized coal pipe
33b: pulverized coal pipe
33c: pulverized coal pipe
33d: pulverized coal pipe
34a: branch pipe
34b: branch pipe
41: pulverized coal concentration adjustment apparatus
42: ribbon screw

BEST MODE FOR CARRYING OUT THE INVENTION

A first embodiment of a pulverized coal concentration adjustment apparatus according to the invention will be described below with reference to FIGS. 1 to 4.

Figure 1:
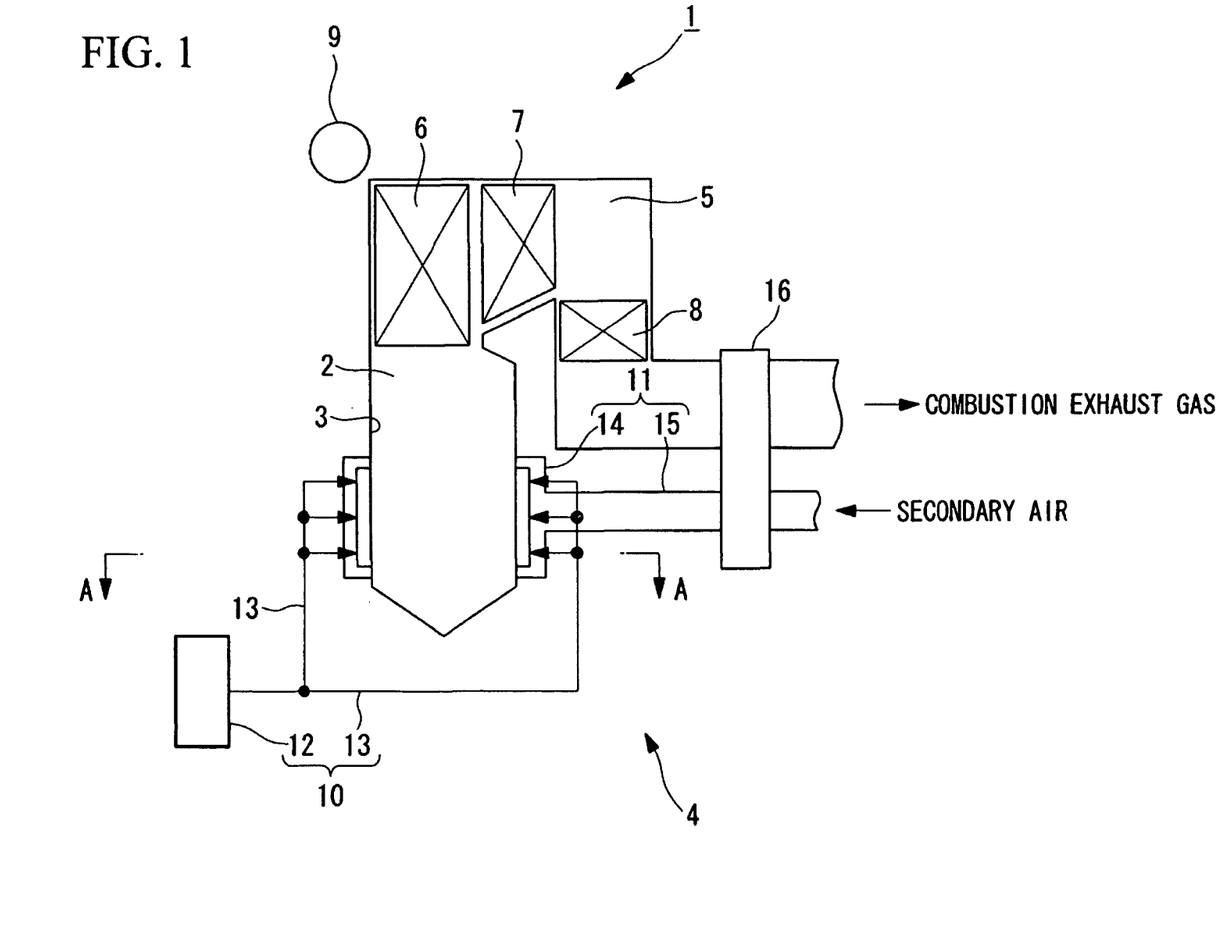
FIG. 1 is a block diagram showing a whole outline construction of a pulverized coal combustion boiler provided with a pulverized coal concentration adjustment apparatus according to a first embodiment of the invention.
Figure 2:
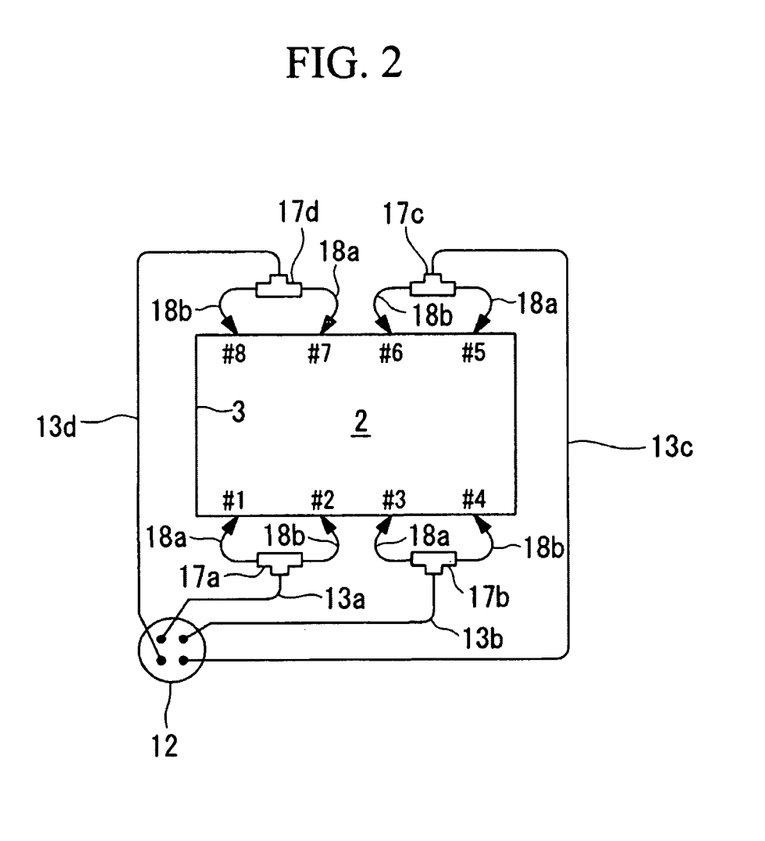
FIG. 2 is a cross sectional view taken along the line A-A in FIG. 1.
Figure 3:
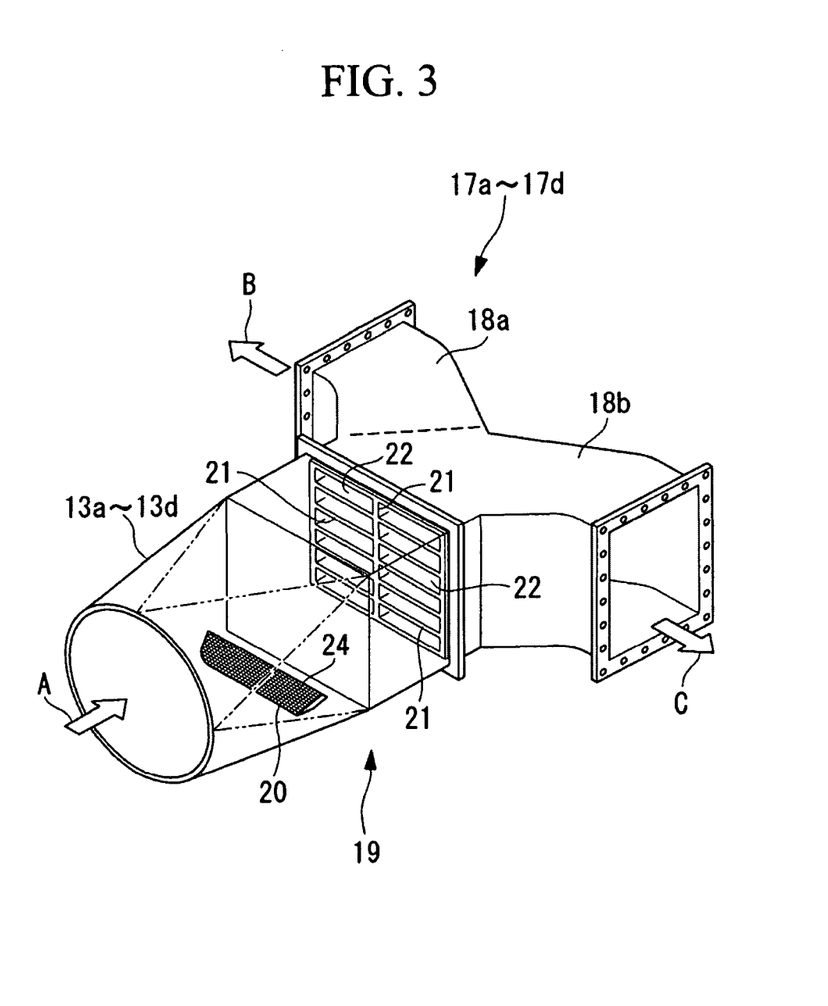
FIG. 3 is a perspective view showing the pulverized coal concentration adjustment apparatus, according to the first embodiment of the invention, as viewed from a side of a pulverized coal pipe.
Figure 4:
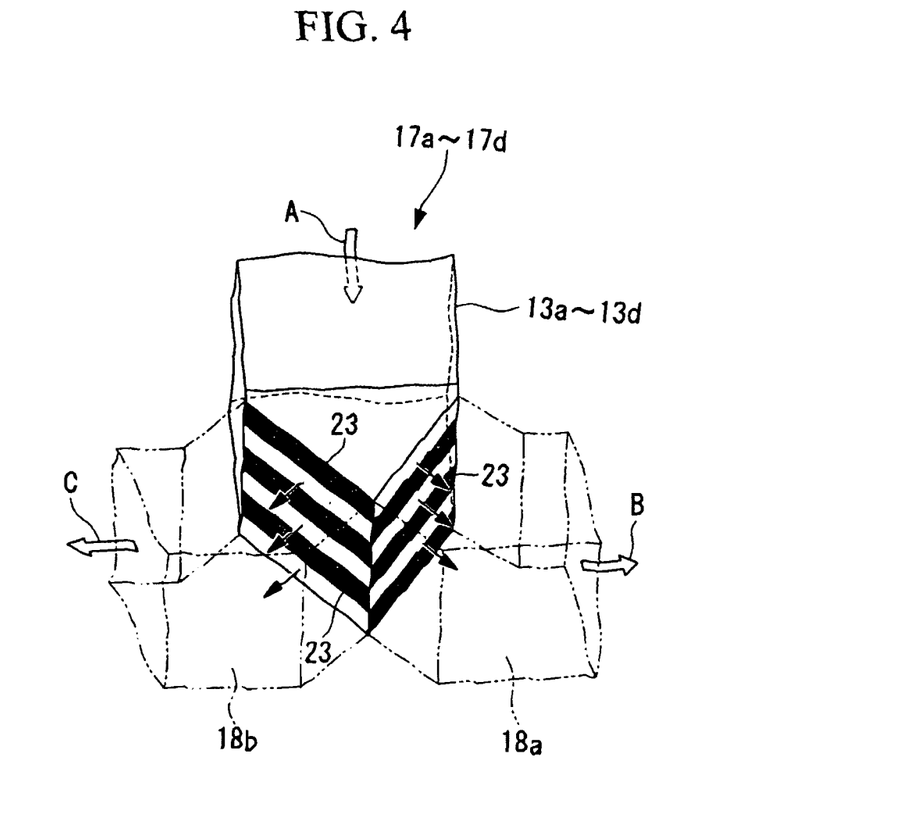
FIG. 4 is a perspective view showing a pulverized coal distributor, according to the embodiment, as viewed from a side of a kiln.

FIG. 1 is a block diagram showing a whole outline construction of a pulverized coal combustion boiler provided with a pulverized coal concentration adjustment apparatus according to the embodiment, FIG. 2 is a cross sectional view taken along the line A-A in FIG. 1, FIG. 3 is a perspective view showing the pulverized coal concentration adjustment apparatus, according to the embodiment, as viewed from a side of a pulverized coal pipe, and FIG. 4 is a perspective view showing a pulverized coal distributor, according to the embodiment, as viewed from a side of a kiln.

As shown in FIG. 1, a boiler 1 includes a kiln 2 mounted in a vertical direction, a combustion apparatus 4 mounted in a lower portion of a kiln wall 3 of the kiln 2, a gas flue 5 connected to an outlet of the kiln 2, a superheater 6 provided extending from an upper portion of the kiln 2 to the gas flue 5, a reheater 7, a coal economizer 8, and a steam drum 9 provided above the kiln 2.

A multiplicity of water tubes (not shown), respectively, are provided inside the kiln wall 3 to extend vertically, the respective water tubes being connected at respective upper and lower ends thereof to the steam drum 9.

The combustion apparatus 4 includes a plurality of pulverized coal burner (not shown) mounted to the kiln wall 3, a pulverized coal supply apparatus 10 for supplying of pulverized coal to the pulverized coal burners, and an air supply apparatus 11 for supplying of secondary air as a combustion air to the pulverized coal burners.

The pulverized coal supply apparatus 10 includes a coal mill (coal pulverizer) 12 for pulverization of coal, which is supplied through a coal feeder (not shown) and a measuring instrument (not shown), to a size (for example, several μm to several hundreds μm) suited to combustion, and a pulverized coal pipe (coal feed pipe) 13 for draft conveyance of pulverized coal, which is generated by the coal mill 12, as a pulverized coal-air mixture to the pulverized coal burners with a conveyance air pressurized and fed from an air source. According to the embodiment, four pulverized coal pipes 13 (pulverized coal 13a, 13b, 13c, 13d) are provided.

Also, the conveyance air is set in terms of safety aspect of the coal mill 12 so that temperature at the outlet of the coal mill 12 becomes about 80° C.

The air supply apparatus 11 includes a forced draft blower (not shown) for pressurization and feeding of an air, a windbox 14 provided on an outer wall of the kiln 2, and an air pipe 15 for connection between the forced draft blower and the windbox 14.

A secondary air passing through the air pipe 15 is caused by a rotary regenerated heat exchanger 16 to perform heat exchange with combustion exhaust gases, temperature of which is, for example, about 360° C. and which pass through the gas flue 5, to be heated to 300° C. to 350° C. to be fed to the windbox 14.

As shown in FIG. 2, pulverized coal burners #1 to #8 are mounted to the kiln wall 3 of the pulverized coal combustion boiler 1. Pulverized coal distributors 17a, 17b, 17c, 17d are provided one by one for the two pulverized coal burners. Pulverized coal is pneumatically conveyed through four pulverized coal pipes 13a, 13b, 13c, 13d to the respective pulverized coal distributors 17a, 17b, 17c, 17d from the coal mill 12. Two branch pipes 18a, 18b are connected to the respective pulverized coal distributors 17a, 17b, 17c, 17d. Pulverized coal pneumatically conveyed to the respective pulverized coal distributors 17a, 17b, 17c, 17d is fed to the respective pulverized coal burners through the branch pipes 18a, 18b provided on the respective pulverized coal distributors 17a, 17b, 17c, 17d. Also, flow sensors (not shown) (for example, the powder flowmeter of Promecon Ltd. in Germany), respectively, are mounted to the branch pipes 18a, 18b to measure the flow rate of pulverized coal passing therethrough.

A pulverized coal concentration adjustment apparatus 19 according to the embodiment includes the pulverized coal distributor 17a, 17b, 17c, 17d and a kicker block 20 (see FIG. 3).

As shown in FIGS. 3 and 4, the pulverized coal distributor 17a, 17b, 17c, 17d are connected to the pulverized coal pipe 13a, 13b, 13c, 13d, through which pulverized coal is pneumatically fed to flow in an arrow A direction, and the branch pipes 18a, 18b, which branch to both left and right sides in a position downstream of the pulverized coal pipe 13a, 13b, 13c, 13d, respectively. A plurality of partition plates 21 are provided in the respective pulverized coal distributors 17a, 17b, 17c, 17d. Interiors of the respective pulverized coal distributors 17a, 17b, 17c, 17d, respectively, are partitioned by the partition plates 21 whereby flow passages 22 in plural stages are formed up and down and left and right in the respective pulverized coal distributors 17a, 17b, 17c, 17d.

Also, as shown in FIG. 4, blank plates 23 are arranged on a downstream side of the flow passage 22. According to the embodiment, the blank plates 23 are arranged alternately on the left and right of the flow passage 22 in a vertical direction. The blank plates 23 cut off communication of the respective flow passages 22 to one of the branch pipes 18a, 18b and flows branched left and right in an arrow B direction and in an arrow C direction pneumatically convey pulverized coal into the branch pipes 18a, 18b.

As shown in FIG. 3, the kicker block (gas-particle flow adjustment device) 20 adjusts the concentration of pulverized coal toward the both left and right branch pipes 18a, 18b positioned on a downstream side. The kicker block 20 is provided in a lower portion of the pulverized coal pipe 13a, 13b, 13c, 13d on an upstream side of inlets of the pulverized coal distributor 17a to 17d.

The kicker block 20 comprises a plate-shaped member arranged along a substantially overall width of the pulverized coal pipe 13a, 13b, 13c, 13d and having a substantially rectangular shape as viewed in plan view. A front (upstream) edge of the kicker block 20 is mounted pivotally to a bottom surface (lower surface) of the pulverized coal pipe 13a, 13b, 13c, 13d. That is, the kicker block 20 is able to swing about the front edge, at which it is connected to the pulverized coal pipe 13a, 13b, 13c, 13d, with the front edge as a fulcrum. The kicker block 20 is formed so that an angle (angle of inclination) $\theta$ between its upper surface and a bottom surface (lower surface) of the pulverized coal pipe 13a, 13b, 13c, 13d can be adjusted in the range of, for example, 0 degree to 60 degrees. The angle $\theta$ can be automatically adjusted on the basis of signals from the flow sensors mounted to the respective branch pipes 18a, 18b by a controller (not shown) so that pulverized coal passing in the branch pipe 18a and pulverized coal passing in the branch pipe 18b are made substantially equal (substantially uniform) in concentration (flow rate) to each other.

Also, an abrasion-resistant material 24 such as ceramic is provided on the upper surface of the kicker block 20 in order to prevent abrasion caused by the passing pulverized coal. The abrasion-resistant material 24 is fixed (anchored) by sticking, for example, a multiplicity of tile pieces, which are formed to be square-shaped, to the upper surface of the kicker block 20 with an adhesive or the like.

Subsequently, an explanation will be given to the action of the pulverized coal concentration adjustment apparatus 19 according to the embodiment.

First, when pulverized coal is fed into the pulverized coal pipes 13a, 13b, 13c, 13d from the coal mill 12 by means of pneumatic conveyance, the pulverized coal flows in the pulverized coal pipes 13a, 13b, 13c, 13d to be directed to the pulverized coal distributors 17a, 17b, 17c, 17d as indicated by the arrow A direction in the figure. At this time, the pulverized coal flows in lower portions of the pulverized coal pipes 13a, 13b, 13c, 13d due to gravitational sedimentation. In this manner, the pulverized coal flowing in the lower portions of the pulverized coal pipes 13a, 13b, 13c, 13d strikes against the upper surface of the kicker block 20 in the vicinity of inlets of the pulverized coal distributors 17a, 17b, 17c, 17d to be rolled upward to flow into the inlets of the pulverized coal distributors 17a, 17b, 17c, 17d while being scattered upward. The pulverized coal as scattered upward is divided (distributed) into the arrow B direction or into the arrow C direction by the pulverized coal distributors 17a, 17b, 17c, 17d and then flows in the downstream branch pipes 18a, 18b to be fed to the pulverized coal burners mounted to the kiln wall 3 to be burnt by the pulverized coal burners.

With the pulverized coal concentration adjustment apparatus 19 according to the embodiment, an angle $\theta$ of the upper surface of the kicker block 20 is automatically adjusted on the basis of signals from the flow sensors mounted to the respective branch pipes 18a, 18b. Thereby, pulverized coal passing in the branch pipe 18a and pulverized coal passing in the branch pipe 18b are made substantially equal (substantially uniform) in concentration to each other, that is, pulverized coal fed to the left and right branch pipes 18a, 18b positioned downstream of the pulverized coal distributor 17a, 17b, 17c, 17d and the respective pulverized coal burners can be uniformly distributed, so that it is possible to reduce NOx and unburned coal.

Also, since the abrasion-resistant material 24 is provided on the upper surface of the kicker block 20, it is possible to improve the kicker block 20 in durability.

Figure 5:
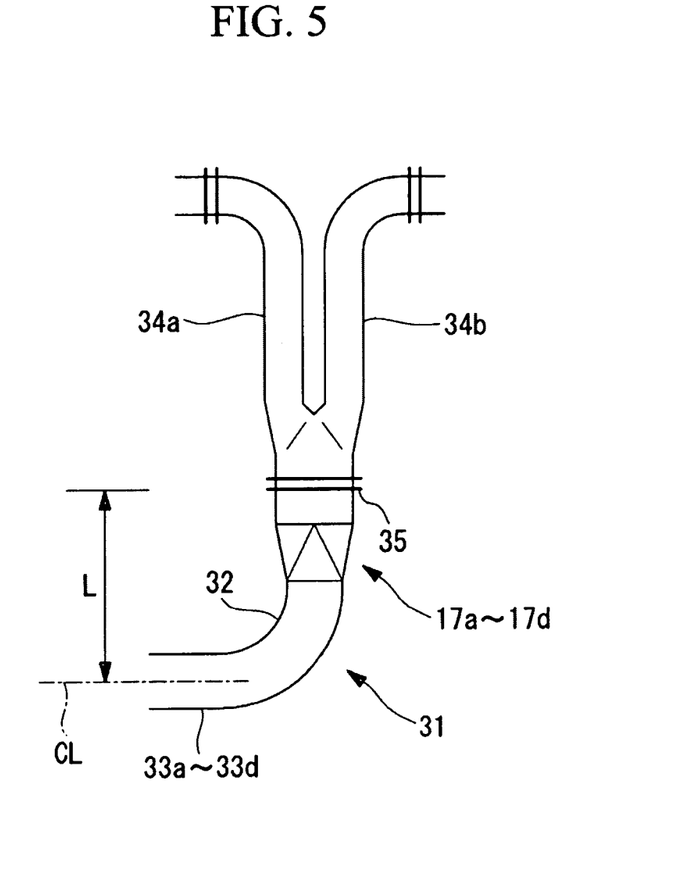
FIG. 5 is a view showing a planar arrangement of a pulverized coal concentration adjustment apparatus according to a second embodiment of the invention.

A second embodiment of a pulverized coal concentration adjustment apparatus according to the invention will be described with reference to FIG. 5. FIG. 5 is a view showing a planar arrangement of the pulverized coal concentration adjustment apparatus according to the embodiment.

The pulverized coal concentration adjustment apparatus 31 according to the embodiment is different from that of the first embodiment in that instead of the kicker block 20 a pulverized coal pipe 33a, 33b, 33c, 33d is provided to arrange each of pulverized coal distributors 17a, 17b, 17c, 17d in a location 10D (D is an inside diameter of the pulverized coal pipe) distant from an elbow (bent portion) 32 of the pulverized coal pipe, more preferably, in the range of 3D to 5D from the elbow 32 of the pulverized coal pipe. Other constituent elements are the same as those of the first embodiment and so an explanation therefor is omitted herein.

In addition, the same members as those of the first embodiment are denoted by the same reference numerals as those of the latter.

As shown in FIG. 5, according to the embodiment, each of the pulverized coal distributor 17a, 17b, 17c, 17d is mounted in a location, in which a horizontal distance (shortest distance) L between a rear end thereof (that is, a portion jointed to branch pipes 34a, 34b) and a central axis CL of the pulverized coal pipe 33a, 33b, 33c, 33d positioned in the vicinity of and on an upstream side of the elbow 32 is equal to or less than 10D (D is an inside diameter of the pulverized coal pipe 33a, 33b, 33c, 33d), more preferably, corresponds to 3D to 5D.

With the pulverized coal concentration adjustment apparatus 31 according to the embodiment, pulverized coal flowing in a lower portion of the pulverized coal pipe 33a, 33b, 33c, 33d on the upstream side of the elbow 32 flows along an inner wall surface of the elbow 32 positioned radially outward to be directed upward from the lower portion of the pulverized coal pipe 33a, 33b, 33c, 33d while being acted by a centrifugal force at the elbow 32. Consequently, the pulverized coal is rolled upward in the vicinity of an outlet (that is, in the vicinity of an inlet of the pulverized coal distributor 17a, 17b, 17c, 17d) of the elbow 32 to flow into the inlet of the pulverized coal distributor 17a, 17b, 17c, 17d while being scattered upward.

Thereby, pulverized coal fed to the left and right branch pipes 34a, 34b positioned downstream of the pulverized coal distributor 17a, 17b, 17c, 17d and the respective pulverized coal burners can be uniformly distributed, so that it is possible to improve the combustion quality (reduction in NOx and unburned coal), thus enabling making boiler water tube temperatures uniform. In addition, the embodiment adopts the branch pipes 34a, 34b, of which pipe length is lengthened corresponding to an extent, by which the pulverized coal distributor 17a, 17b, 17c, 17d is mounted close to the elbow 32 of the pulverized coal pipe 33a, 33b, 33c, 33d. When such branch pipes 34a, 34b are adopted, however, pulverized coal distributed uniformly passes in the branch pipes 34a, 34b, so that such adoption of the branch pipes 34a, 34b does not affect uniformization of distribution of the pulverized coal.

Figure 6:
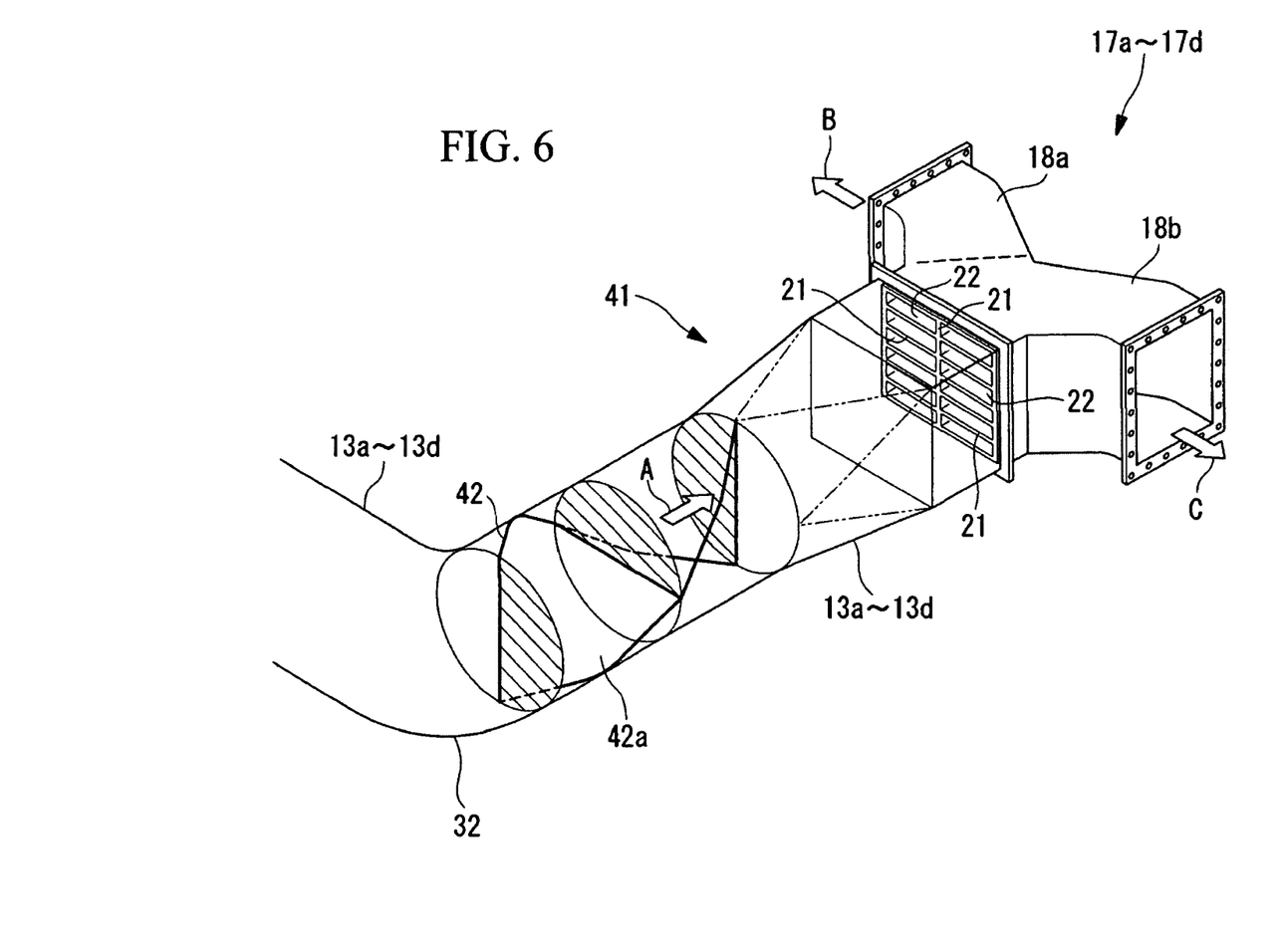
FIG. 6 is a perspective view showing a pulverized coal concentration adjustment apparatus, according to a third embodiment of the invention, as viewed from a pulverized coal pipe.

A third embodiment of a pulverized coal concentration adjustment apparatus according to the invention will be described with reference to FIG. 6. FIG. 6 is a perspective view showing the pulverized coal concentration adjustment apparatus, according to the embodiment, as viewed from a pulverized coal pipe.

The pulverized coal concentration adjustment apparatus 41 according to the embodiment is different from that of the first embodiment in that a ribbon screw 42 is provided instead of the kicker block 20. Other constituent elements are the same as those of the first embodiment and so an explanation therefor is omitted herein.

In addition, the same members as those of the first embodiment and the second embodiment are denoted by the same reference numerals as those of the latter.

As shown in FIG. 6, the ribbon screw 42 is a thin plate member, which divides a flow passage in a pulverized coal pipe 33a, 33b, 33c, 33d into two halves so as to make flow passage areas thereof substantially equal to each other. The ribbon screw 42 is arranged so as to have one end (upstream end) thereof positioned in the vicinity of an outlet of an elbow 32 and to have the other end (downstream end) thereof positioned in the vicinity of an inlet of a pulverized coal distributor 17a, 17b, 17c, 17d. Also, one end and the other end of the ribbon screw 42, respectively, are arranged to agree substantially with a perpendicular (vertical) axis, which passes a central axis of the pulverized coal pipe 33a, 33b, 33c, 33d. The ribbon screw 42 is twisted to lead pulverized coal, which flows along an inner wall surface of the elbow 32 positioned radially outward in the elbow 32, upwardly of the pulverized coal pipe 33a, 33b, 33c, 33d to lead the same to one side (leftward as viewed from an upstream side) of the pulverized coal pipe 33a, 33b, 33c, 33d.

With the pulverized coal concentration adjustment apparatus 41 according to the embodiment, pulverized coal flowing in a lower portion of the pulverized coal pipe 13a, 13b, 13c, 13d on the upstream side of the elbow 32 flows along an inner wall surface of the elbow 32 positioned radially outward while being acted by a centrifugal force at the elbow 32. Thereafter, the pulverized coal is given a whirling force (counter-clockwise torque as viewed from the upstream side) when passing between a surface 42a of the ribbon screw 42 and an inner wall surface of a pulverized coal pipe 13a, 13b, 13c, 13d positioned downstream of the elbow 32, and flows into the inlet of a pulverized coal distributor 17a, 17b, 17c, 17d while being scattered radially outward.

Thereby, pulverized coal fed to left and right branch pipes 18a, 18b positioned downstream of the pulverized coal distributor 17a, 17b, 17c, 17d and respective pulverized coal burners can be uniformly distributed, so that it is possible to improve the combustion quality (reduction in NOx and unburned coal), thus enabling making boiler water tube temperatures uniform.

In addition, the invention is not limited to the embodiments described above but can be changed, modified, and embodied within a scope not departing from the gist of the invention. For example, the kicker block 20 described in the first embodiment is also applicable to the second embodiment or the third embodiment.

Also, the embodiments have been described with respect to an arrangement, in which the two branch pipes 18a, 18b, 34a, 34b are connected to the downstream side of the pulverized coal distributor 17a, 17b, 17c, 17d. However, the invention is not limited thereto but applicable to that arrangement, in which three or more branch pipes are connected to the downstream side of the pulverized coal distributor 17a, 17b, 17c, 17d.

The invention claimed is:

1. A pulverized coal concentration adjustment apparatus comprising
    a pulverized coal distributor, of which an upstream end is connected to a pulverized coal pipe, through which pulverized coal is pneumatically conveyed to flow, and a downstream end is connected to a plurality of branch pipes, and which distributes and pneumatically conveys the pulverized coal to the respective branch pipes through flow passages in plural stages, and
    a gas-particle flow adjustment device provided on an upstream side of the pulverized coal distributor and at a bottom in the pulverized coal pipe to adjust pulverized coal to the branch pipes in concentration, and
    wherein the gas-particle flow adjustment device comprises a plate-shaped member provided along a substantially overall width of the pulverized coal pipe to have a substantially rectangular shape as viewed in plan view, an upstream leading edge of the gas-particle flow adjustment device is mounted pivotally to a bottom surface of the pulverized coal pipe, and an angle formed between an upper surface of the gas-particle flow adjustment device and a bottom surface of the pulverized coal pipe can be automatically adjusted on the basis of signals from flow sensors mounted to the respective branch pipes.

2. A pulverized coal combustion boiler comprising the pulverized coal concentration adjustment apparatus according to claim 1.

\* \* \* \* \*